(12) United States Patent
Glazier et al.

(10) Patent No.: US 6,214,811 B1
(45) Date of Patent: Apr. 10, 2001

(54) ACYCLOVIR DIESTER DERIVATIVES

(75) Inventors: Arnold Glazier; Milka Yanachkova; Ivan Yanachkov, all of Newton, MA (US)

(73) Assignee: Drug Innovation & Design, Inc., Waltham, MA (US)

( * ) Notice: Subject to any disclaimer, the term of this patent is extended or adjusted under 35 U.S.C. 154(b) by 0 days.

(21) Appl. No.: 09/514,552

(22) Filed: Feb. 28, 2000

Related U.S. Application Data

(63) Continuation of application No. 09/080,064, filed on May 15, 1998, now Pat. No. 6,031,096, which is a continuation-in-part of application No. 09/050,220, filed on Mar. 27, 1998, now abandoned, which is a continuation of application No. 08/857,150, filed on May 15, 1997, now abandoned.

(51) Int. Cl.[7] ............................. A61K 31/675; C07F 9/65
(52) U.S. Cl. ............................................. 514/81; 544/244
(58) Field of Search ................................................ 514/81

(56) References Cited

U.S. PATENT DOCUMENTS

| | | | |
|---|---|---|---|
| 4,146,715 | 3/1979 | Schaeffer | 544/279 |
| 4,199,574 | 4/1980 | Schaeffer | 424/200 |
| 4,294,831 | 10/1981 | Schaeffer | 424/253 |
| 4,323,573 | 4/1982 | Schaeffer | 424/253 |
| 4,806,642 | 2/1989 | Sircar et al. | 544/244 |
| 4,816,447 | 3/1983 | Ashton et al. | 514/81 |
| 4,845,084 | 7/1989 | Hannah et al. | 514/81 |
| 5,055,458 | 10/1991 | Bailey et al. | 514/81 |
| 5,580,571 | 12/1996 | Hostetler | 424/443 |
| 5,627,185 | 5/1997 | Glazier | 514/269 |
| 5,789,589 | 8/1998 | Glazier | 544/244 |
| 6,031,096 | * 2/2000 | Glazier et al. | 544/244 |

FOREIGN PATENT DOCUMENTS

| | | |
|---|---|---|
| 0143987 | 6/1985 | (EP) . |
| WO 90/08128 | 7/1990 | (WO) . |
| WO 91/19721 | 12/1991 | (WO) . |
| WO 96/40088 | 12/1996 | (WO) . |
| WO 97/40056 | 10/1997 | (WO) . |

OTHER PUBLICATIONS

Welch, C.J., et al., "The Chemical Synthesis and Antiviral properties of an Acyclovir–Phospholipid Conjugate," Acta Chemica Scandinavica, B39; 47–54 (1985).

* cited by examiner

Primary Examiner—Mukund J. Shah
Assistant Examiner—Pavanaram K Sripada
(74) Attorney, Agent, or Firm—Hamilton, Brook, Smith & Reynolds, P.C.

(57) ABSTRACT

Disclosed are novel prodrugs represented by the following structural formula;

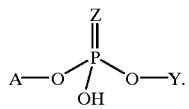

Z is oxygen or sulfur; Y is, together with a hydroxy group, acyclovir or an analog of acyclovir; A is a substituted benzyl group with one or more protected hydroxy or protected amine groups in the ortho or para positions, relative to the phosphate ester, which can be converted in vivo to a hydroxy or amino group. Also disclosed is a method of treating a viral infection in an individual or animal. The method comprises administering to the individual or animal a therapeutically effective amount of a prodrug represented by structural formula shown above.

20 Claims, 3 Drawing Sheets

ACYCLOVIR DIESTER DERIVATIVES

RELATED APPLICATIONS

This application is a continuation of U.S. Ser. No. 09/080,064, filed on May 15, 1998, now U.S. Pat. No. 6,031,096, which is a continuation-in-part of U.S. Ser. No. 09/050,220, filed on Mar. 27, 1998 abandoned, which is a continuation of U.S. Ser. No. 08/857,150, filed on May 15, 1997 abandoned, the entire teachings of which are incorporated herein by reference.

BACKGROUND

Antiviral agents currently in use are of limited effectiveness in treating dermal infections caused by viruses. For example, herpes simplex labialis, commonly referred to as "cold sores" do not respond to the topical treatment with acyclovir (Spruance et al., *Am. J. Med.,* 73(1A):315–319 (1982); Shaw et al. , *Br. Med. J. (Clin. Res. Ed.*), 291(6487): 7–9 (1985); Raborn, et al., *Oral Surg. Oral Med. Oral Pathol.,* 67(6):676–679 (1989); Spruance, et al., *Antimicrob. Agents Chemother.,* 25(5):553–555 (1984); Raborn, et al., *J. Can. Dent. Assoc.,* 55(2):135–137(1989)). Oral administration of acyclovir for the treatment of cold sores is only partially effective (Spruance et al., *J. Infect. Diseases* 161:185 (1990)).

The limited effectiveness of antiviral agents such as acyclovir applied topically to cold sores and other dermal viral infections is thought to be a consequence of the limited ability of most of these agents to penetrate the skin (Parry, et al.,*J. Invest. Dermatol.,* 98(6):856–863 (1992); Spruance, et al., *Antimicrob. Agents Chemother.,* 25(1):10–15 (1984)). Topical treatments for genital herpes infections are also ineffective for the same reason. Consequently, there is a need for new antiviral agents which can penetrate the skin and which are active against viruses which cause dermal infections.

SUMMARY OF THE INVENTION

Lipophilic phosphotriester prodrugs of acyclovir, as disclosed in U.S. Ser. No. 08/635,653, filed Apr. 22, 1996, (the entire teachings of which are hereby incorporated by reference), are extremely active topically against herpes virus infection. The present invention is based on the discovery that the corresponding phosphodiester prodrugs of acyclovir, which are nonlipophilic and water soluble, are even more effective antiviral drugs than phosphotriesters and more effective than acyclovir. For example, treatment of guinea pigs with dermal herpes simplex virus-1 (HSV-1) infections with Prodrug 1 and Prodrug 2 resulted in a dramatic reduction in lesion number, in lesion area and in lesion virus titer (Examples 1 and 3) when compared to its vehicle. In contrast, comparable treatment with U.S. ZOVIRAX (acyclovir) provided results that were statistically the same as with placebo.

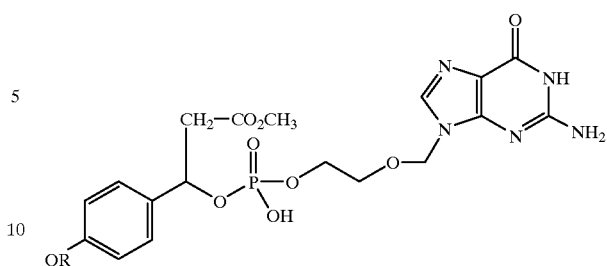

1) $R = -CO-C(CH_3)_3$
2) $R = -CO-CH_3$

In one embodiment, the present invention is a prodrug of acyclovir, an analog of acyclovir, acyclovir monophosphate or an acyclovir monophosphate analog. The prodrug is represented by Structural Formula (I):

(I)

and physiologically acceptable salts thereof.

Z is oxygen or sulfur, preferably oxygen.

Y is, together with a hydroxy group, acyclovir or an analog of acyclovir.

A is a substituted benzyl group with one or more protected hydroxy or protected amine groups in the ortho or para positions, relative to the phosphate ester, which can be converted in vivo to a hydroxy or amino group.

Another embodiment of the present invention is a method of treating a viral infection in an individual or animal. The method comprises administering to the individual or animal a therapeutically effective amount of a prodrug represented by Structural Formula (I).

Another embodiment of the present invention is a method of preparing the prodrugs of the invention and intermediate used in the synthesis of phosphate ester prodrugs, including the diester prodrugs represented by Structural Formula (I), phosphotriester prodrugs disclosed in U.S. Ser. No. 08/310,972, filed Sep. 23, 1994, and the phosphotriester prodrugs disclosed in U.S. Ser. No. 08/635,553. The intermediate is represented by Structural Formula (II):

(II)

Y' is, together with a hydroxy group, a nucleoside analog, preferably acyclovir or an acyclovir analog.

A is a substituted benzyl group with one or more protected hydroxy or protected amine groups in the ortho or para positions, relative to the phosphate ester, which can be converted in vivo to a hydroxy or amino group.

The method for preparing the intermediate comprises reacting Y'-OH, a weak anhydrous organic acid such as tetrazole and $(A-O)_2$-P $(NR_{21}R_{22})$ in an aprotic, polar organic solvent. Suitable aprotic, polar organic amide solvents include dialkyl amide solvents (e.g., dimethylformamide (DMF) or N,N-dimethylacetamide), tetraalkylurea solvents (e.g., 1,3-dimethylimidazolinone or 1,3-dimethyl-3,4,5,6-tetrahydro-2(1H)-pyrimidinone); dialkyl sulfoxide solvents (e.g., dimethylsulfoxide and tetramethylene sulfoxides) and phosphoramide solvents (e.g., hexamethylphosphoramide). Preferred solvents are dialkyl amides. DMF is most preferred. $R_{21}$ and $R_{22}$ are each independently a lower alkyl, an aryl group or, taken together with the phosphoramide nitrogen, can form a five, six or seven membered nitrogen-containing heterocyclic ring (preferably a saturated heterocyclic ring). The lower alkyl, aryl or heterocyclic compound represented by $R_{12}$ and $R_{22}$ can optionally be substituted with one or more groups which do not react (or are subtantially inert) with the P—N bond or with the weak acid. Preferred examples of substituents include non-nucleophilic, non-basic inert groups such as halides, (lower alkyl)—O—, lower alkyl and aryl. Preferably, $R_{21}$ and $R_{22}$ are each a lower alkyl group such as ethyl.

The phosphodiester acyclovir prodrugs disclosed herein are more active against dermal herpes simplex virus 1 infections than acyclovir or the phosphotriester prodrugs of acyclovir disclosed in U.S. Ser. No. 08/635,553. In addition, the phosphodiester prodrugs of acyclovir disclosed herein are chemically more stable, have longer shelf lives and are generally easier to formulate than the phosphotriester prodrugs disclosed in U.S. Ser. No. 08/635,553.

DETAILED DESCRIPTION OF THE INVENTION

Figure 1A:
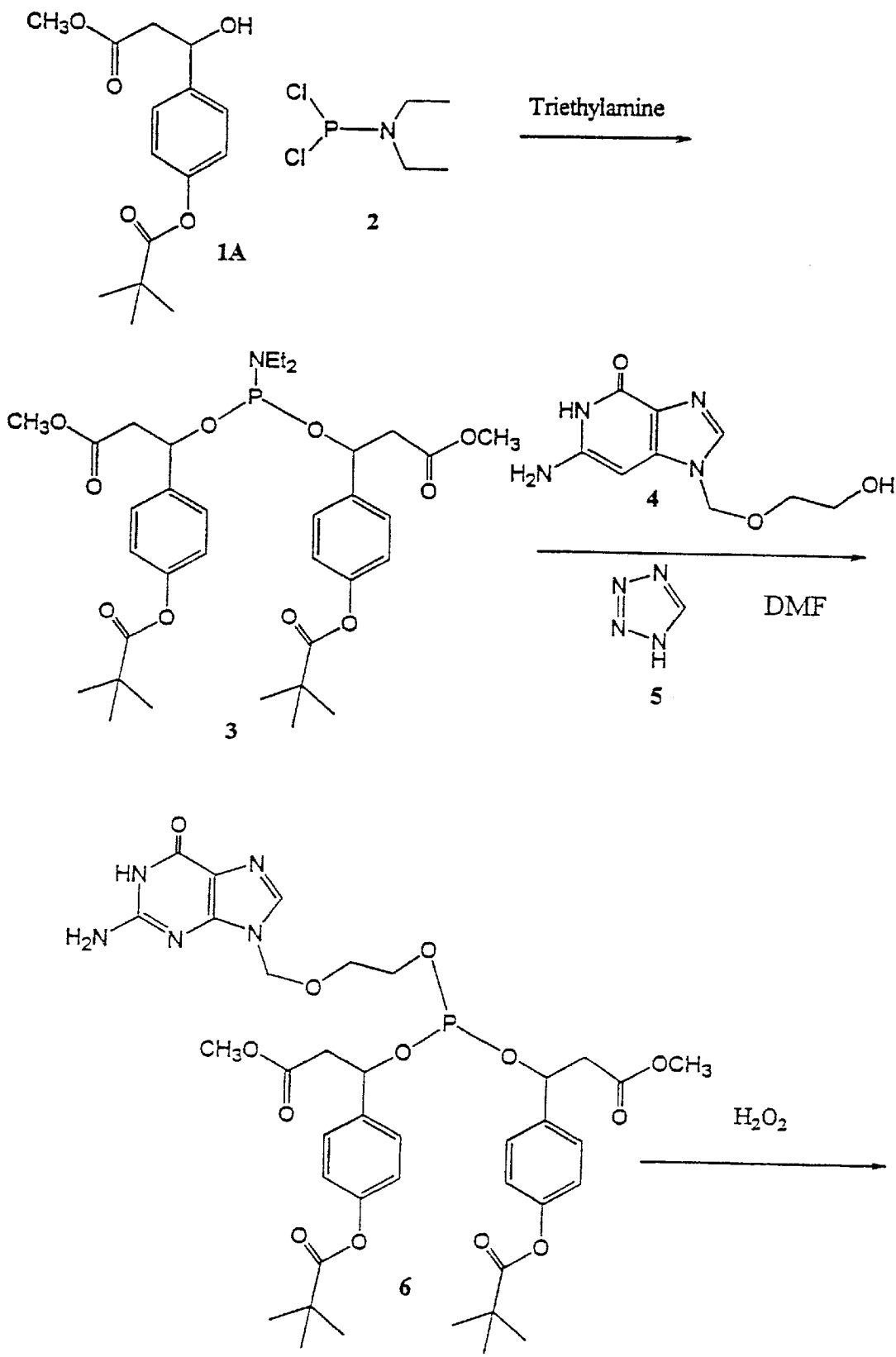
FIGS. 1A and 1B represent a schematic showing a synthetic scheme used to prepare Prodrug 1.

Disclosed herein are novel prodrugs of drugs such as acyclovir, which are nucleoside analogs. The disclosed prodrugs show increased effectivenes compared with the parent drugs. Also described are improved methods of preparing phosphate triester prodrugs of nucleoside analogs. These methods are also useful in the preparation of the disclosed phosphodiester prodrugs.

The effectiveness of antiviral agents such as acyclovir and acyclovir analogs can be enhanced by converting the agent into a phosphorus containing prodrug represented by Structural Formula (I). Phosphorus containing prodrugs are described in U.S. Ser. Nos. 08/635,553, 07/714,130, 07/537,332 and 08/310,972, the entire teachings of which are hereby incorporated into this application by reference.

A prodrug, as used herein, is an agent which can be metabolized in vivo, i.e. undergoes biotransformation, to give the pharmacologically active agent or a monophosphate of the pharmacologically active agent. "Metabolized" refers to chemical or biochemical reactions which the prodrug undergoes in vivo. Examples include enzyme catalyzed reactions and reactions which occur in solution such as solvolysis, hydrolysis and elimination reactions.

Use of a prodrug for treating an individual can have advantages over the parent drug, e.g. greater lipophilicity to enhance delivery of the pharmacologically active agent across cell membranes or into the stratum corneum of the skin. Accordingly, lipid solubility is a desirable property for antiviral drugs. The prodrugs of the present invention have a lipophilic portion that allows the prodrug to penetrate into the stratum corneum of the skin and yet are charged molecules which are highly soluble in water and which can be transformed in vivo into acyclovir, an analog of acyclovir, acyclovir monophosphate or an analog of acyclovir monophosphate.

As used herein, an "acyclovir analog" is an antiviral purine with a substituted alkyl group (e.g., a C3 to about a C12 substituted alkyl group) bonded to nitrogen nine. As used herein, a "purine" has a pyrimidine ring fused to an imidazole ring. It will be understood that tautomeric forms of a purine are also included, such as in the structure shown for Prodrug 1. Examples of purines include adanine and guanine.

The carbon atoms of the purine can be bonded to or substituted by, for example, a hydrogen, halogen, hydroxy, (lower alkyl)—O—, thio, (lower alkyl)thio, amino, (lower alkyl)amino, di(lower alkyl)amino, (lower alkyl)—CO—NH— or azide.

The alkyl or substituted alkyl group bonded to nitrogen nine of the purine (nitrogen nine is indicated in Structural Formula (III) can optionally have an ether, thioether or amine moiety linkage within the chain and is straight chained or branched. The substituted alkyl group can have one or more substituents, such as, hydroxy, amino, —NH (lower alkyl), (lower alkyl)—O—, (substituted lower alkyl)—O—, aryl, substituted aryl, aryloxy, substituted aryloxy, (lower alkyl)NH—SO$_2$—O—, (substituted lower alkyl)NH—SO$_2$—O—, (aryl)NH—SO$_2$—O—, (substituted aryl)NH—SO$_2$—O—, phosphate, —NH—CO—(lower alkyl), —NH—CO—(substituted lower alkyl), —NH—CO—aryl, —NH—CO—(substituted aryl), (lower alkyl)—CO—, (substituted lower alkyl)—CO—, —CO—aryl and —CO—(substituted aryl). Lower alkyl, substituted lower alkyl, aryl and substituted aryl are defined hereinbelow.

In a preferred embodiment, an "acyclovir analog" is represented by structural Formula (III):

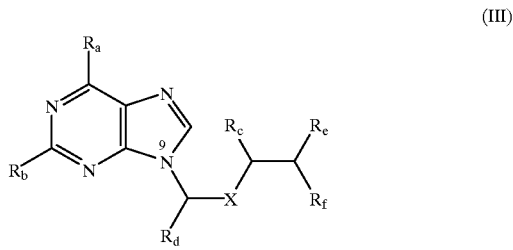

(III)

X is sulphur, —NH—, —N(lower alkyl)—, or oxygen;

$R_a$ is hydrogen, halogen, hydroxy, (lower alkyl)—O—, azide, thio, (lower alkyl)thio, amino, (lower alkyl)amino or di(lower alkyl)amino;

$R_b$ is hydrogen, halogen, (lower alkyl)thio, (lower alkyl)—CO—NH— (referred to herein as "acylamino"), amino or azide;

$R_c$ is hydrogen, lower alkyl, substituted lower alkyl, aryl, substituted aryl. Aryl is preferably phenyl;

$R_d$ is hydrogen, lower alkyl and substituted lower alkyl;

$R_e$ is hydrogen, lower alkyl, substituted lower alkyl, aryl, substituted aryl, (lower alkyl)O—, (substituted lower alkyl) O—, aryloxy and substituted aryloxy; and $R_f$ is hydroxy.

In a preferred embodiment, Y is represented by Structural Formula (IV):

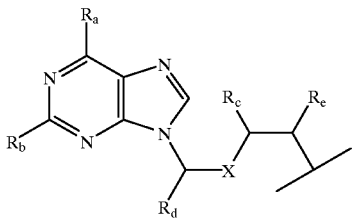
(IV)

As seen from Structural Formula (IV), when acyclovir or an acyclovir analog is used to form a prodrug of the present invention, $R_f$ in Structural Formula (III) is a covalent bond between acyclovir or the acyclovir analog and an oxygen bonded to a phosphorus atom of the prodrug. For example, in Structural Formula (I) $R_f$ is a covalent bond between Y and an oxygen bonded to phosphorus, referred to herein as a "phosphoester bond". The covalent bond between A and O is also a phosphoester bond.

Specific examples of suitable acyclovir analogs are provided in U.S. Pat. Nos. 4,199,574, 4,294,831 and 4,323,573, the entire teachings of which are hereby incorporated into this patent application by reference.

In a preferred embodiment, $R_a$ is —OH, $R_b$ is —NH$_2$ and X is oxygen. It is most preferred that $R_c$, $R_d$, and $R_e$ are each —H and $R_f$ is a phosphoester bond between Y and an oxygen of the phosphate of the prodrug, i.e. Y, together with a hydroxy group, is acyclovir.

The following is a description of the present invention with respect to prodrugs comprising phosphate groups, e.g., prodrugs represented by Structural Formula (I).

A is a group which can be metabolized in vivo to give a chemically modified A (A'). As a result of the biotransformation, the phosphoester of the prodrug which comprises modified A (A') undergoes cleavage in vivo. Cleavage of the phosphoester can result, for example, from the heterolytic cleavage of the oxygen-carbon bond of the phosphoester group comprising a modified A (A'). In this instance, the phosphate acts as a leaving group. Cleavage in vivo of a phosphoester comprising modified A (A') will be enhanced relative to a phosphoester comprising A if biotransformation in vivo results in a greater electron density on the carbon atom to which the phosphate is bonded in modified A (A') than on the carbon atom to which the phosphate is bonded in A.

For example, a compound having a structure represented by Structural Formula (I) will be cleaved more rapidly in vivo when A is a benzyl with an electron donating group in the ortho or para position than when A is an unsubstituted benzyl group. Thus, A can be, for example, a substituted benzyl group that undergoes biotransformation in vivo such that groups already present at the ortho and/or para positions are converted into groups that are more strongly electron donating in modified A (A') than in A.

Protected hydroxy groups such as acyloxy groups (e.g., lower alkyl—CO—O— and aryl—CO—O—), carbonate groups (e.g., —O—CO—O—lower alkyl and —O—CO—O—aryl), carbamate groups (e.g., —O—CO—NH—lower alkyl and —O—CO—NH—aryl) and protected aryl amine groups such as acylamine groups (e.g., lower alkyl—CO—NH— and aryl—CO—NH—) are only very slightly electron donating, but can be converted (e.g. unmasked) in vivo into the strongly electron donating hydroxy or amino groups, respectively. For example the Hammett para sigma+constant for the acetoxy group and the acetyl amino group are −0.06 and −0.60, respectively. In contrast, the hydroxy group and the amino group are strongly electron donating. The Hammett para sigma+constant for the hydroxy and amino groups are −0.92 and −1.7, respectively. The ionized hydroxy group (—O—) is even more electron donating with a Hammett para sigma+constant that has been estimated at −2.3. Chapman, N. B. and Shorter, J., *Correlation Analysis in Chemistry,* Plenum Press, N.Y., N.Y., page 483–484; Vogel, P., Carbocation Chemistry, Elsevier, N.Y., N.Y. (1985) page 243; Hansch, C., *Comprehensive Medicinal Chemistry,* Pergamon Press, N.Y., N.Y., 4:235.

The unmasking of a phenol can be carried out in vivo by enzymes. For example, nonspecific esterase is ubiquitous within the cytoplasm of cells and is able to cleave a wide variety of carboxylate esters. Phenolic carbonates and carbamates are degraded by cellular enzymes to yield-phenols (Ditter et al., *J. Pharm. Sci.* 57:783 (1968); Ditter et. al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988)). The unmasking of a phenol can also occur by hydrolysis. For example, a wide variety of carbonate and carbamate groups are known which undergo spontaneous cleavage in solution at kinetically favorable rates (Saari et al., *J. Med. Chem.* 33:97 (1990) and Rattie et al., *J. Pharm. Sci.* 59:1741 (1970)). When A is a substituted benzyl group, cleavage of, for example, a (lower alkyl)—CO—O—, —O—CO—O—(lower alkyl) or —O—CO—NH—(lower alkyl) group in the ortho or para position to give a modified A (A') will trigger heterolytic fission of the C—O bond between modified A (A') and the oxygen of the phosphate. Based on the above considerations the conversion of, for example, an ortho and/or para (lower alkyl)—CO—O—, —O—CO—O—(lower alkyl) or —O—CO—NH—(lower alkyl) group into a hydroxy group will lead to a rate increase of phosphoester fission of at least 7000 fold. If the resulting hydroxy group is ionized to an oxyanion, O−, the rate of solvolysis can be further increased about $2 \times 10^{10}$ fold. Based on an intracellular pH of 7 and a pKa of 10 for the phenolic hydroxy group about 0.1% of the hydroxy groups will be ionized under physiological conditions. The net result is that overall a rate increase on the order of $2 \times 10^7$ fold can occur in the heterolytic cleavage of the C—O bond between modified A (A') and the oxygen of the phosphoester following cleavage of an ortho or para acyloxy group in A by nonspecific esterase.

In a preferred embodiment, the prodrugs of the present invention are synthesized by replacing one of the hydroxy groups on the phosphorous atoms of the monophosphate parent drug with a group "A—O—", wherein the group "A" is a substituted benzyl derivative with one or more protected hydroxy groups (e.g., (lower alkyl)—CO—O—, aryl—CO—O, —O—CO—O—(lower alkyl), —O—CO—O—aryl, —O—CO—NH—(lower alkyl) and —O—CO—NH—aryl) or protected amine groups (e.g., (lower alkyl)—CO—NH—, (aryl)—CO—NH—, (lower alkyl)—O—CO—NH—, aryl—O—CO—N—, (lower alkyl)—NH—CO—N— and aryl—NH—CO—NH—) in ortho or para positions relative to the phosphoester. The monophosphate of the parent drug is liberated following conversion of the protected hydroxy group or protected amino group into the corresponding hydroxy group or amino group, respectively. The monophosphate of the parent drug can be converted to the parent drug by the action of enzymes such as alkaline phosphatases.

Preferably, A is a substituted benzyl group which is further substituted at the benzylic position by a moiety which facilitates cleavage of the phosphoester bond. Suitable substituents at the benzylic position include groups which are capable of stabilizing a carbon cation formed upon cleavage of the phosphoester bond, for example, a lower alkyl group.

More preferably, A is substituted at the benzylic position by a moiety such that cleavage of the phosphoester bond between A or A' and the phosphate oxygen will result in an elimination reaction to form a double bond between the benzylic carbon and the moiety. Suitable moieties generally comprise a methylene or methine group, wherein said methylene or methine group is 1) bonded to the benzylic position of A and 2) has an acidic hydrogen. Upon cleavage of the phosphoester in vivo, A or A' can then undergo an elimination reaction by loss of the phosphate bonded to the benzylic carbon and the acidic hydrogen to form a carbon-carbon double bond at the benzylic position. Alternatively or additionally, a preferred prodrug of the invention is degraded to acyclovir monophosphate or an analog of acyclovir monophosphate by an elimination reaction triggered by the spontaneous or enzymatic unmasking of a strongly electron donating group, such as a hydroxy or amino group at the ortho or para positions of a benzyl group represented by A.

Suitable moieties at the benzylic carbon of the A include those having an electron withdrawing group bonded to the methylene or methine group with the acidic hydrogen (see March, Advanced Organic Chemistry, John Wiley & Sons, third edition (1985) page 884), for example —CHR'-Z, wherein Z is an electron withdrawing group such as —COOR", —COR", —CONH$_2$, —CONHR", —NO$_2$, —SO$_2$R" and —CN.

R' is —H, a lower alkyl group, substituted lower alkyl group, aryl or a substituted aryl.

R" is —H, a lower alkyl group, a substituted lower alkyl group, an aryl group or a substituted aryl group. In one example, Z is —COOR", wherein R" is —H, methyl, ethyl, n-propyl, iso-propyl, n-butyl, sec-butyl or t-butyl. In another example, R" is —(CH$_2$)$_n$CH$_3$, wherein n is 5, 6, 7, 8, 9, 10, 11, 12, 13, 14, 15, 16, 17, 18, 19 or 20, Preferably, A is represented by the Structural Formula (V):

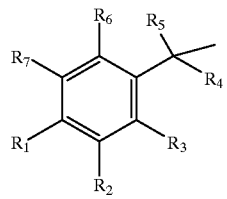

(V)

$R_1$, $R_3$ or $R_6$ are independently selected from the group consisting of —O—CO—$R_8$, —O—CO—O$R_8$, —O—C(O)—NH$R_8$, —O—C(O)—N($R_8$)$_2$, —NH—CO—$R_8$, —NH—CO—O$R_8$, —NH—CO—NH$R_8$, and an inert group, with the proviso that at least one of $R_1$, $R_3$ or $R_6$ is not an inert group.

$R_2$ and $R_7$ are independently an acyloxy group —H, (—O—CO$R_8$) or an inert group.

$R_4$ and $R_5$ are independently selected from the group consisting of hydrogen, a lower alkyl group, a substituted lower alkyl group and a moiety such that cleavage of the phosphoester bond between A or A' and a phosphate oxygen results in an elimination reaction to form a carbon-carbon double bond between the benzylic position of A or A' and the moiety.

$R_8$ is selected from the group consisting of a lower alkyl group, a substituted lower alkyl group, an aryl group, a substituted aryl group and a group such that the resulting ester moiety is degraded to the free phenolic hydroxy group in vivo. Preferably, $R_8$ is selected from the group consisting of methyl, ethyl, n-propyl, iso-propyl, n-butyl, sec-butyl, t-butyl, n-pentyl or n-hexyl. Other examples include —CHR$_9$—NHR$_{10}$, —CH(OR$_{11}$)—CH$_3$, CH$_3$O—(CH$_2$)$_2$—O—(CH$_2$)$_2$—O—CH$_2$—, CH$_3$O—(CH$_2$)$_2$-O—CH$_2$—, —OCH$_3$, —CH$_2$—CO—CH$_3$ and —CH$_2$(OR$_{11}$), wherein $R_9$ is the side chain of an amino acid, $R_{10}$ is H or an amine protecting group and $R_{11}$ is H or an alcohol protecting group. Suitable protecting protecting groups can be selected by the skilled artisan and are described in Green and Wuts, *"Protecting Groups in Organic Synthesis"*, John Wiley and Sons, Chapters 5 and 7, 1991, the teachings of which are incorporated herein by reference.

The nature of the labile groups at $R_1$, $R_3$, and $R_6$ determines the rate at which the resulting prodrug is transformed to the parent phosphorus bearing drug. The solubility of the prodrug can be varied by changing the nature of the groups $R_1$–$R_8$. Water solubility can be enhanced by selecting substituents with hydrophilic groups such as —CH$_2$OH or —CO$_2$H. Alternatively, one can select bulky substituents which can increase lipid solubility.

In an even more preferred embodiment, the prodrug is represented by the following structural formula:

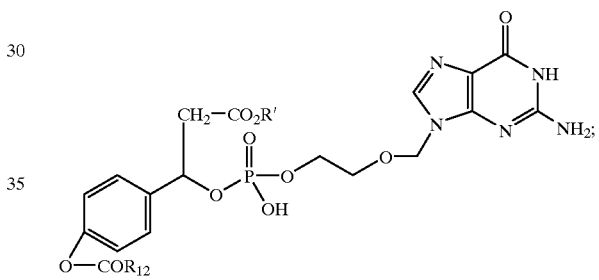

or physiologically acceptable salts thereof;

wherein $R_{12}$ and R' are each independently lower alkyl or substituted lower alkyl. $R_{12}$ can also be CH$_3$—CO—CH$_2$—, CH$_3$O—(CH$_2$)$_2$—O—(CH$_2$)$_2$—O—CH$_2$—, CH$_3$O—(CH$_2$)$_2$—O—CH$_2$— and —OCH$_3$. Preferably, R' can also be —H. $R_{12}$ and R' are each independently selected from the group consisting of —H, methyl, ethyl, n-propyl, iso-propyl, n-butyl, sec-butyl, t-butyl, n-pentyl, n-hexyl. R' is even more preferably methyl.

The prodrugs of the present invention are degraded in vivo and in blood to the acyclovir. Without being limited to a particular reaction the mechanism by which the prodrugs are believed to undergo transformation to the monophosphate of the parent drug is shown in the scheme below:

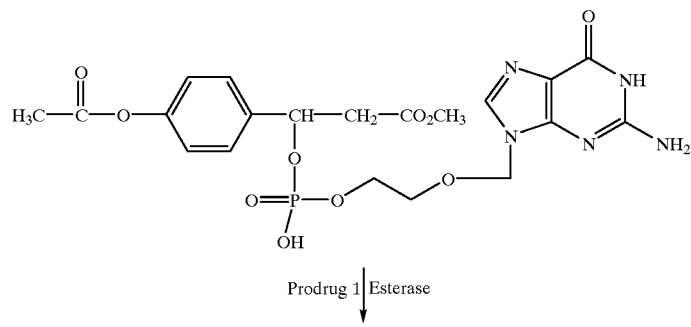

Prodrug 1 | Esterase

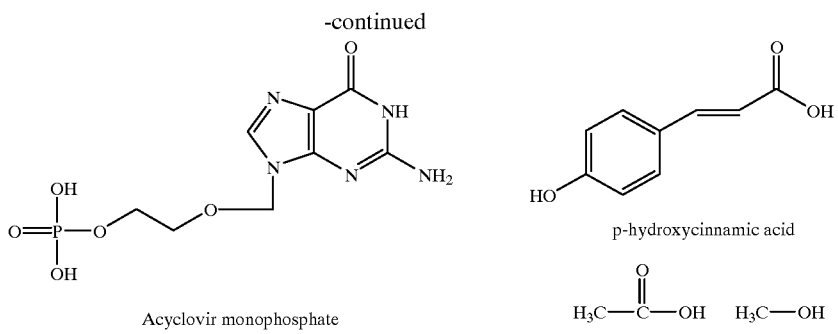

Acyclovir monophosphate p-hydroxycinnamic acid $H_3C-\overset{\overset{O}{\|}}{C}-OH$   $H_3C-OH$ When incubated with pig liver esterase in phosphate buffered $D_2O$, NMR results show that Prodrug 1 is degraded to acyclovir monophosphate and p-hydroxycinnamic, as shown in the Scheme above. This assay is described in Glazier, WO 91/19721 entitled "Phosphorus Prodrugs" and can be used to determine suitable hydroxyl or amino protecting groups which can be cleaved in vivo. The entire teachings of WO 91/1972 are incorporated herein by reference. It is to be understood that there are other in vitro assays known to one of ordinary skill in the art employing esterases, amidases or enzymes capable of cleaving carbonate, carbamate, ester and amide groups which can also be used to determine suitable protecting groups.

In the above description the term "inert" is used-to refer to groups that are substantially nonreactive and do not influence in a major fashion the chemistry of the prodrug metabolism or decay. Examples of inert groups include —H, lower alkyl, substituted lower alkyl, aryl, substituted aryl, halogen, —COO(lower alkyl), (lower alkyl)—O—, (substituted lower alkyl)—O— (e.g. benzyloxy and substituted benzyloxy), —CO—(lower alkyl), —CO—(substituted lower alkyl), —CO—(aryl), —CO—(substituted aryl), —CHO, —CN and —$NO_2$.

As used herein, a "lower alkyl" group can have from 1 to about 20 carbon atoms, preferably 1 to 6 carbon atoms, and can be straight chained, branched or cyclic. In addition, a "lower alkyl" group can have one or more double and/or triple bonds. An "aryl" group includes a heterocyclic or carbocyclic aromatic group such as phenyl and naphthyl. Heterocyclic atomatic groups include, for example, imidazolyl, indolyl, thienyl, furanyl, pyridyl, pyranyl, pyranyl, oxazolyl, benzothienyl, benzofuranyl, quinolinyl, isoquinolinyl and acridintyl.

Suitable substituents on a lower alkyl, an aryl group and a benzyl group include inert substituents, as described above.

Suitable physiological salts of the prodrugs of acyclovir and acyclovir analogs disclosed herein are those which are non-toxic. Examples include, but are not limited to, sodium, potassium, calcium, magnesium, ammonium monoalkylammonium, dialkylammonium, trialkylammonium, diethanol ammonium and triethanol ammonium, salts of the disclosed prodrugs. These salts can be prepared by an exchange reaction with a salt of the desired cation with an appropriate anion, including halides, —$ClO_4^-$, acetate, or other alkanoates or aryl carboxylates. These salts can also be prepared with an ion exchange resin loaded with the desired cation.

Procedures for preparing phosphate ester prodrugs of nucleoside analogs (e.g., acyclovir) include using phosphoamidites in conjunction with H-tetrazole (see Perich and Johns, *Synthesis* 1988:142). These procedures are described in U.S. Ser. Nos. 07/714,130, 07/537,332 and 08/310,972, the entire teachings of which have been incorporated into this application by reference. However, these procedures suffer from a number of shortcomings. Nucleoside analogs such as acyclovir are insufficiently soluble in the organic solvents normally used for this reaction, e.g., methylene chloride, chloroform, acetonitrile, tetrahydrofuran and pyridine. As a result, the nucleoside analog (e.g., acyclovir) must be protected to enhance its solubility and prevent side reactions, thereby increasing the cost of preparing phosphate ester prodrugs. Alternative methods have been reported which use phosphorus oxychloride in conjunction with trimethyl or triethyl phosphate as solvent (see U.S. Pat. No. 4,287,188). However, trialkyl phosphates are toxic carcinogens with alkylating activity. Accordingly, their use on an industrial scale is problematic.

Figure 2:
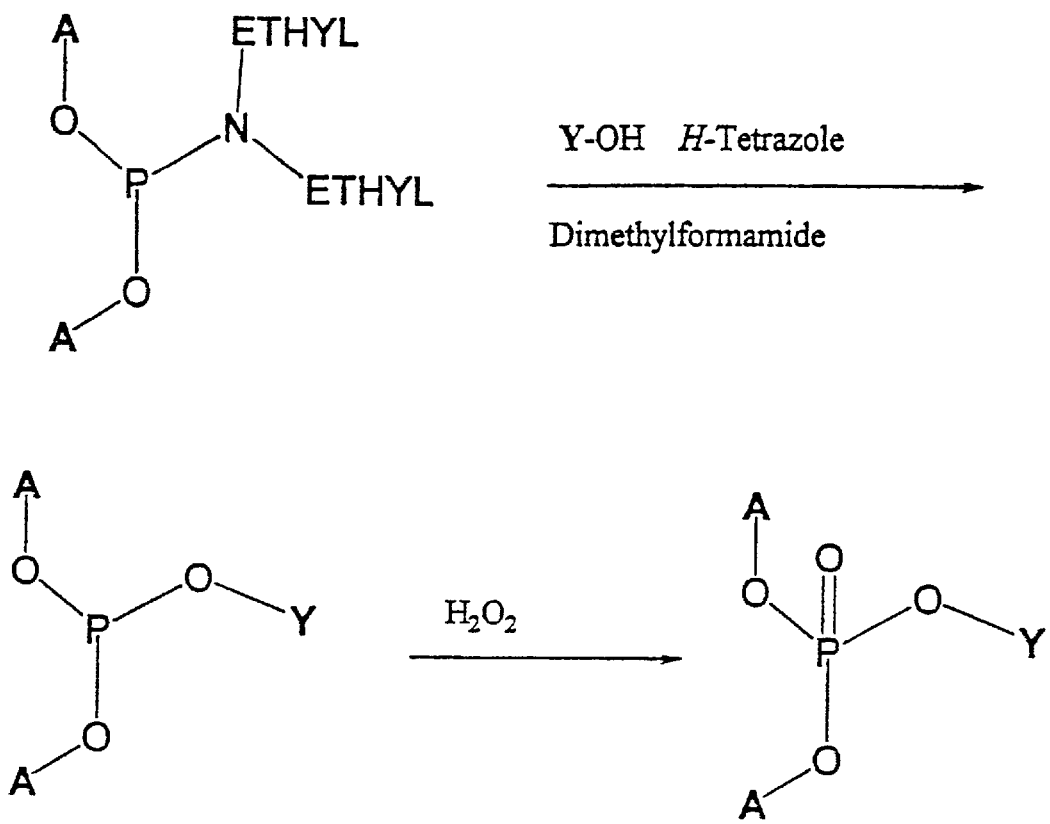
FIG. 2 is a schematic showing the synthesis of phosphate triesters by reacting the nucleoside analog Y—OH, (A—O)$_2$—P—N—(ethyl)$_2$ and tetrazole in a dimethylformamide and oxidizing the resulting phosphite triester product with hydrogen peroxide.

Described below are novel synthetic methods for preparing phosphate esters prodrugs of nucleoside analogs which overcome these disadvantages. Using these methods, phosphate esters prodrugs of nucleoside analogs such as acyclovir can be prepared in nearly quantitative yield without protecting acyclovir or the nucleoside analog. Acyclovir or a nucleoside analog Y'—OH suspended in an aprotic polar organic solvent reacts rapidly and quantitatively with phosphoramidites (A—O)$_2$—P—(NR$_{21}$,R$_{22}$) in the presence of a weak anhydrous organic acid to produce the corresponding phosphite ester, which can be oxidized without isolation with a phosphite oxidizing agent to the corresponding phosphate triester. This reaction sequence is shown schematically in FIG. 2. The phosphate triester can be converted to the diester prodrug in the presence of a base, for example, an amine base such as triethyl amine.

A "nucleoside analog" is a drug whose activity is a consequence of its structural similarity to a nucleoside. In a target organism, the drug can be erroneously incorporated into biological molecules such as DNA or RNA. Biomolecules incorporated with nucleoside analogs do not undergo the same biochemical reactions as the corresponding naturally-occurring biomolecules. As a result, the nucleoside analog toxic to the target organism. Nucleoside analogs suitable for use in the present invention (Y'—OH) have a free hydroxyl group. Examples include 3'-azido-thymidine (AZT), 2'3'-didehydro-2'3'-dideoxythymidine (D4T), 2'3'-dideoxyadenosine and trifluorothymidine.

Suitable weak anhydrous organic acids include acids suitable for use in the synthesis of polynucleotides by phosphoramidate methodology, which are well known in the art. Generally weak anhydrous organic acids having a pKa from about 2 to about 6 are preferred, for example, H-tetrazole, 1-H-triazole and 3-nitro-1-H-triazole.

About a 10–20% molar molar excess of the weak acid and nucleoside analog-with respect to the phosphoramide is generally used. However, it is also possible to use equimolar amounts of the three reagents or about a three fold or more excess of any one or two of these reagents. Suitable concentrations for the reagents range from about 0.05 M to about 2.0 M and typically range from about 0.3 M to about 1.3 M. The reaction can be generally carried out at temperatures ranging from −10° C. to about 80° C., but typically at room temperature. Reactions can be monitored by thin layer chromotagraphy to determine reaction times. Polar co-solvents such as pyridine, acetonitrile, methylene chloride and chloroform can be added in amounts which do not significantly decrease the solubility of the nucleoside analog or the reaction rate.

The oxidation of the phosphite ester can be carried out with from about 1.0 to about 3.0 equivalents of the phosphite oxidizing agent (e.g., hydrogen peroxide) at temperatures ranging from about 0° C. to about 50° C. Preferably, the reaction is carried out with about a 10–15% excess of phosphite oxidizing agent at about 10–20° C. Preferably, the oxidation can be performed without isolating the phosphite ester intermediate.

A "phosphite oxidizing agent" is a reagent which oxidizes phosphite esters to phosphate esters. Phosphite oxidizing agents are known in the art of oligonucleotide synthesis and include hydrogen peroxide, peracids such as meta chloroperbenzoic acid, iodine in water and nitrogen tetraoxide. Hydrogen peroxide is preferred.

Phosphate triesters containing acyclovir, an analog of acyclovir or a nucleoside analog can be converted to phosphate diester prodrugs by reacting the phosphate triester with a suitable base, e.g., a base which can cause an elimination reaction with an ester substituted in the beta position with $(RO)_2PO-O-$, wherein R is a substituted or unsubstituted alkyl, aryl or heteroaryl group. Examples of suitable bases include, but are not limited to, hydroxide, amines (e.g., ammonia, an alkyl amine, a dialkyl amine or a trialkyl amine), alkoxides and hydride bases (e.g., sodium or potassium hydride). At least one equivalent of, base per mole of phosphate triester is generally used. When an amine is used as the base, the reaction mixture can contain up to about 50% amine base by volume in a suitable organic solvent, preferably between about 20% to about 30%. The reaction can be carried out between about 0° C. and about 50° C., preferably at room temperature. Suitable solvents are those in which both the base and the phosphate triester are soluble and compatible (e.g., do not react with the base) and are readily determined by the person of ordinary skill in the art. For example, when an amine is used as the base, suitable solvents generally include polar solvents such as acetonitrile, methylene chloride, chloroform and nitromethane; alcohols can be used with alkoxide bases; etheral solvents can be used with hydride or amide bases.

Procedures for preparing the disclosed diester prodrugs are shown in FIG. 1 and described in detail in Example 2. It is to be understood that certain modifications in these procedures may be required. For example, changes in the reaction conditions used may be necessary when different A or Y groups are used. The selection of suitable reaction conditions is within the ability of one skilled in the art of organic chemistry.

The prodrugs of the subject application can be used to treat infections in individuals (e.g., humans and animals). caused by various classes of DNA and RNA viruses, including cytomegalovirus, adenovirus (in particular adenovirus 5) rhino virus, Mengo virus, Sinbis virus and vaccinia virus. They are especially active against herpes viruses, including simplex, zoster and varicella, and, in particular, for dermal herpes simplex virus-1 infection. Animals which can be treated by the prodrugs of the present invention include veterinary animals, such as dogs, guinea pigs, cats and the like, and farm animals, such as cows, horses, pigs, goats, sheep and the like.

A "therapeutically effective amount" of a prodrug is an amount of prodrug which decreases the duration and/or severity of a viral infection in an individual or animal. Alternatively, a "therapeutically effective amount" comprises an amount of prodrug which lowers the virus titer in an individual or animal with a viral infection or which ameliorates the symptoms and/or discomfort associated with the viral infection. In the case of dermal viral infections, including herpes simplex virus-1, a "therapeutically effective amount" of a prodrug is an amount which decreases lesion number, lesion area and/or virus titer in the skin of an infected individual or animal.

The skilled artisan will be able to determine the precise amount of prodrug to be administered to an animal or an individual. The amount of prodrug that is administered to an individual will depend on a number of factors including the general health, size, age and sex of the animal or individual and the route of administration. It will also depend on the degree, severity and type of viral infection. One of ordinary skill in the art will be able to determine the precise dosage according to these and other factors. Typically, between about 0.01 mg/kg body weight per day and about 200 mg/kg body weight per day are administered to the individual or animal.

The prodrug can be administered orally, for example, in capsules, suspensions or tablets. Other modes of parenteral administration which can be used include systemic administration, such as by intramuscular, intravenous, subcutaneous, or intraperitoneal injection. In the case of a virus infection in the skin, for example a dermal herpes simplex virus-1 infection, the prodrug is preferably applied topically directly to skin which shows symptoms of viral infection.

The prodrug can be administered to the individual or animal in conjunction with an acceptable pharmaceutical carrier as part of a pharmaceutical composition for treating viral infections. Suitable pharmaceutical carriers may contain inert ingredients which do,.not interact with the prodrug. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986)

For topical administration for the treatment of viral infections in the skin, the pharmaceutical compositions, in addition to the prodrug, can additionally comprise an inert, non-toxic solvent such as water, acetone, an alcohol, or mixtures thereof, in which the prodrug is dissolved, or, preferably, a pharmaceutical carrier suitable for local topical administration in which the prodrug is dissolved or suspended. Examples of pharmaceutically acceptable carriers include, for example, commercially available inert gels, or liquids supplemented with albumin, methyl cellulose or a collagen matrix. Typical of such formulations are ointments, creams and gels. Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration. Creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia-colloidal clays, beegum, and the like. Upon formation of the emulsion, the active ingredients are added in the desired concentration. Gels are comprised of a base selected from an oleaginous base, water, or an emulsion-suspension base, as previously described. To the base can be added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

The invention is further illustrated by the following examples, which are not intended to be limiting in any way.

EXAMPLE 1

Acyclovir Prodrug 1 is more Effective in Reducing Dermal HSV-1 Virus Infection than Acyclovir Formulation The formulation for Prodrug 1 contained 5% EL-620 EMULPHOR (polyoxyethylated castor oil) (Rhone Poluenc), 5% CARBOPOL (Carboxypolymethylene, sodium salt) (B. F. Goodrich), 10% ethanol and 2% by weight Prodrug 1. The balance of the formulation consisted of water.

EL-620 EMULPHOR and water were mixed and ultrasonicated to give a clear emulsion, to which the ethanol was added. The prodrug was then added, and the mixture was ultrasonicated. The sodium carbopol was then added to the emulsion and mixed until to homogeneity.

The placebo was prepared identically to the pharmaceutical compositions except that the prodrugs were omitted.

The pharmaceutical compositions were stored at room temperature.

Animal Inoculation and Subsequent Treatment with Prodrug 1

Female Hartley outbred guinea pigs, 400 to 450 grams, were obtained from Charles River Breeding Labs, Wilmington, Mass. Animals were anesthetized with 25 mg/kg ketamine and 5 mg/kg xylazine SQ. Hair on the dorsum from the shoulders to the rump was removed with electric clippers followed by two 5–10 minute applications of a chemical depilatory. A grid of four areas was demarcated with a pen on both sides of the spine at levels corresponding to mid back and rump.

Undiluted HSV-1 virus stock (0.035 ml) was applied to each different area and introduced through the skin at well-spaced sites at ten activations of a six-pronged spring-loaded vaccination instrument (Sterneedle, Pan Ray Division, Ormont Drug, Englewood, N.J.). The day of inoculation is Day 0. Approximately 250 mg of drug or placebo was applied to the areas according to the dosing regimen on Days 1, 2 and 3. Eight guinea pigs were used during the experiments allowing eight comparisons between each drug and its placebo.

On Day 4 regrown hair on the dorsum of the guinea pigs was removed with one 3–4 minute application of a chemical depilatory. HSV lesions were counted and Polaroid pictures of the animals' backs were taken. The animals were sacrificed using $CO_2$ gas and the full thickness skin of the back was removed by dissection. The square of the skin from each of the four treatment areas was placed into 15 mls of tissue culture medium with 2% FES in an ice bath. The samples were then homogenized in a stomacher Lab Blender 80 (Tekmar Co.). Debris was pelleted by centrifugation and the supernatants collected and frozen at −70° C. until assay for infectivity by plaque formation in VERO cells.

Results

The mean and standard deviation for number of lesions, total lesion area and lesion virus titer were computed. Paired data (drug/vehicle) were evaluated by the Wilcoxon signed-rank test using percent differences between $log_{10}$ derivatives of mean lesions severity at drug-treated sites compared to the Vehicle-treated sites.

U.S. ZOVIRAX ointment applied four times per day is devoid of activity and is not statistically different from placebo. In contrast, Prodrug 1 resulted in a 72% reduction in lesion number, 79% reduction in lesion area and 93% reduction in skin viral titers compared with placebo ($p<0.01$).

EXAMPLE 2

Synthesis of the Acyclovir Prodrugs

A. Synthesis of Methyl (4-Hydroxybenzoyl)acetate

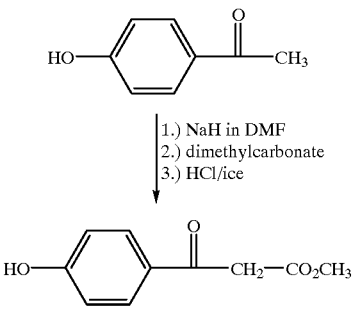

Apparatus:

3L, 3 neck round bottom flask, mechanical stirrer, addition funnel thermometer, cooling bath, Argon bubbler.

Procedure:

Sodium hydride (60% dispersion in mineral oil, 74.0 grams, 1.85 moles) was suspended under anhydrous argon in petroleum ether (250 ml), left to settle down and the solvent was removed under argon. The procedure was repeated with another portion (250 ml) of petroleum ether. 250 ml of anhydrous DMF was added.

A solution of 4'-hydroxyacetophenone (50.4 grams, 0.37 moles) in 250 ml dimethylformamide (DMF) was added drop wise to the suspension of NaH over a 1.5 hour period and the temperature was kept below 32° C. by intermittent cooling with ice an bath. When the addition was completed, the reaction mixture was stirred for 15 minutes until the gas evolution had subsided and the temperature dropped to 28° C. Dimethylcarbonate (167.0 grams, 1.85 moles) was added drop wise over 1 hour and the temperature was maintained below 35° C.

The reaction mixture was stirred at room temperature under argon for 36 hours. The reaction mixture was cooled with an ice bath and poured with stirring into a mixture of ice (1.5 L volume), water (1.0 liter) and concentrated HCl (170 mL) and extracted with ethylacetate (4×250 ml). Combined ethylacetate extracts were washed with water (1×200 ml), 5% citric acid (2×200 ml), 5% NaHCO₃ (2×200 ml), water (2×200 ml), dried over Na₂SO₄ and concentrated on rotary evaporator.

The residual oil was crystallized from toluene/hexane. Yield 63 gm –89%.

The reaction and work up were monitored by TLC in 40% ethylacetate in hexane.

B. Synthesis of Methyl [4-(2,2,2-Trimethylacetoxybenzoyl)acetate]

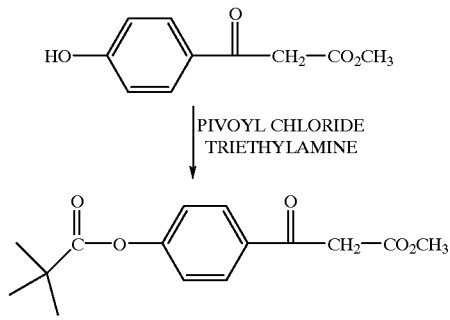

To a stirred and cooled solution of methyl (4-hydroxybenzoyl)acetate (20 grams, 0.103 moles) in 150 ml anhydrous chloroform and triethylamine, (15.8 ml, 11.4 grams, 0.113 moles) a solution of trimethylacetyl chloride (13.6 grams, 0.113 moles) in 20 ml chloroform was added drop wise over 15 minutes.

When the addition was completed, the ice bath was removed and the reaction mixture was stirred at room temperature for 2 hours.

The reaction mixture was washed with water (3×100 ml), 5% NaHCO₃ (3×100 ml), water (1×100 ml), dried over Na₂SO₄ and the solvent removed on rotary evaporator. The residue was purified by crystallization from diethyl ether/petroleum ether.

C. Synthesis of Methyl 3-hydroxy-3-[4-(2,2,2-Trimethylacetoxy)-phenyl] propionate (Alcohol 1A)

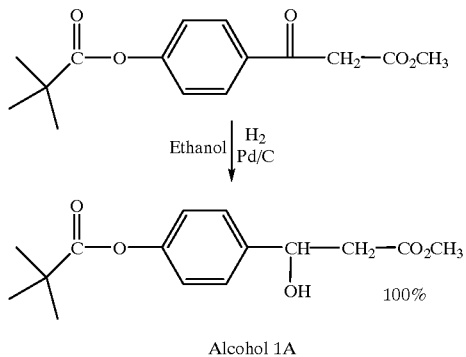

Alcohol 1A

A Parr apparatus was charged with methyl [4-(2,2,2-trimethylacetoxybenzoyl)acetate] (13.0 grams, 46.7 moles), ethanol (100 mL), water (50 mL) and 0.8 grams of 10% Palladium on activated carbon. The mixture was reacted for eight hours with stirring under a H₂ atmosphere at 40 psi, filtered and evaporated to dryness. The residue was recrystallized from toluene/petroleum ether to give alcohol 1A (12.83 grams, 98%).

D. Preparation of the Phosphoramide Intermediate 3

Figure 1B:
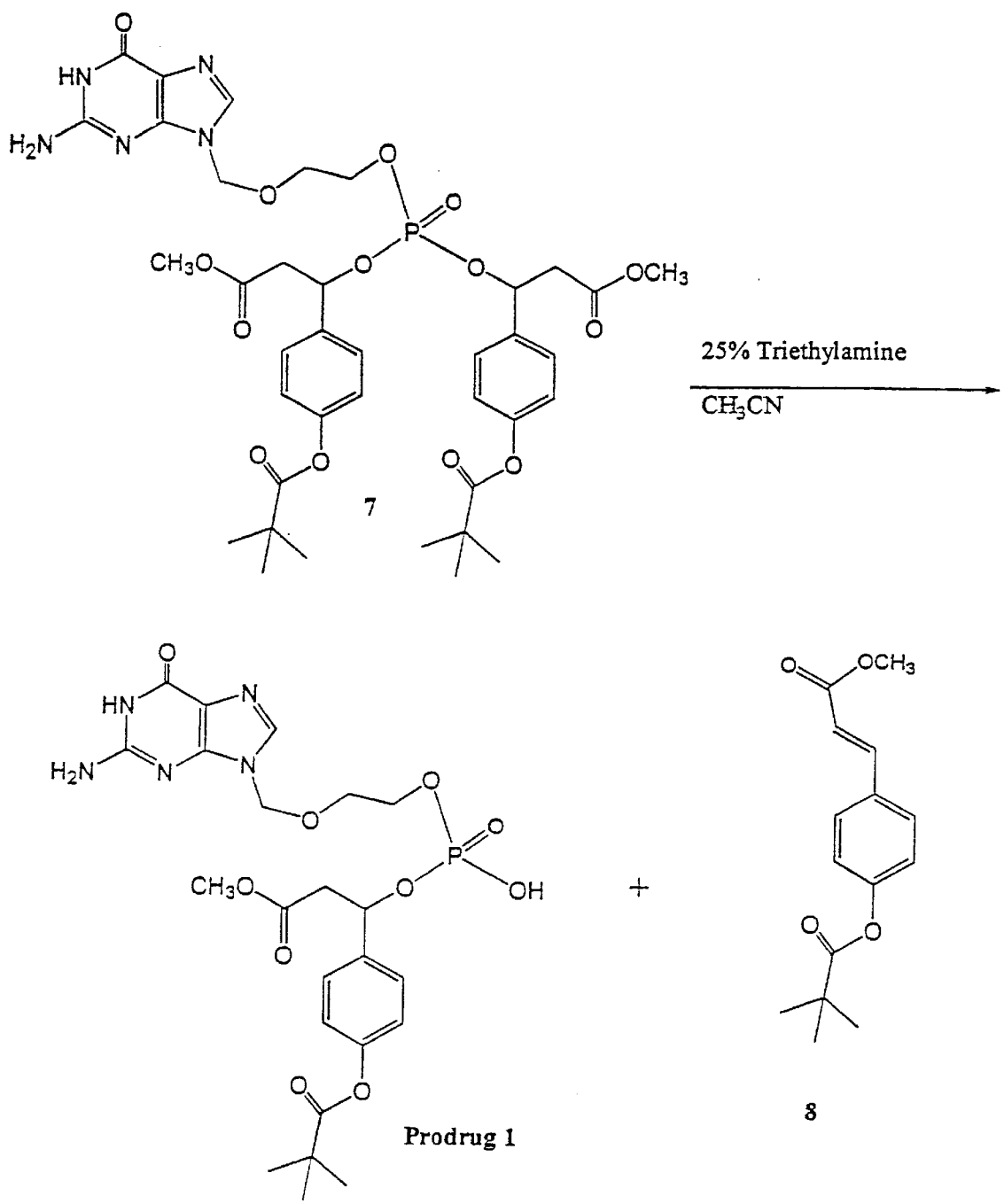

Referring to FIGS. 1A and 1B, alcohol 1A (28.03 g, 0.1 mol) and a stirring bar were loaded in a 500 mL round bottom flask. The flask was sealed with a rubber septum and flashed with nitrogen. Dry THF (150 mL) was added by a syringe followed by triethylamine (10.12 g, 14.0 mL, 0.1 mol). The mixture was stirred under nitrogen until alcohol 1A dissolved and then cooled in an ice bath. Diethylphosphoramidous dichloride 2 (8.70 g, 7.30 mL, 0.05 mol) was weighed with a syringe and added dropwise with stirring over about 5 minutes. After 15 minutes the ice bath was removed and the reaction mixture stirred for 24 hours. At that point a TLC in EtOAc/hexane 40:60 showed no starting material (UV detection). The mixture was filtered under a blanket of nitrogen and the flask and solid were washed with 3×25 mL THF. The combined filtrate and washings were evaporated on a rotary evaporator equipped with a dry-ice cooled condenser at a bath temperature of 25° C. to afford Intermediate 3 as an oil.

E. Preparation of Phosphite Triester Intermediate 6

The flask with Intermediate 3 was equipped with a stirring bar and sealed with rubber septum. Dry DMF (45 mL) was added and the mixture was stirred until the oil dissolved. Acyclovir 4 (9.38 g, 0.0417 mol) and then 1H-tetrazole (3.50 g, 0.05 mol) were added quickly and the resulting suspension was stirred sealed under nitrogen for 24 hours. After about 2 hours, acyclovir 4 dissolved and the reaction mixture became clear. TLC after 24 hours in chloroform/methanol/water 50:10:1 showed complete consumption of the acyclovir 4. Comparable results were obtained when 1,3-dimethyl-2-imidozolidinone was used in place of DMF.

F. Oxidation of Phosphite Triester Intermediate 6 to Phosphate Triester 7

The reaction mixture was cooled with an ice bath and hydrogen peroxide (30% w/w solution in water, 6.80 g, 5.2 mL, 0.06 mole) was added with stirring. The rate of addition was adjusted so that the temperature remained below 15° C. When the exothermic reaction subsided the bath was removed and the mixture was left at room temperature for 1.5 hours.

The reaction mixture was cooled on an ice bath and Na₂SO₃ (2.52 g, 0.02 mmol) dissolved in 8 mL of water was added with stirring. The rate of addition was adjusted so that the temperature remained below 15° C. The mixture was left at room temperature for 25 minutes and then evaporated under vacuum (0.7–0.5 mm Hg) on rotary evaporator equipped with a dry ice cooled condenser at a bath temperature of 25° C. The residue was dissolved in 100 mL of methylene chloride, filtered and loaded on a column of silica gel (420 g, ~900 mL dry volume) equilibrated with methylene chloride- The column was eluted with methylene chloride (2 L) until UV absorption of the eluate returned to the initial value. This step eluted less polar impurities. The column was further eluted with methylene chloride/methanol 15:1 (6 L) until UV absorption returned to the initial value. 200 mL fractions were collected. Fractions 13–25 were pooled and evaporated to afford a white foam. This residue was dried overnight under vacuum (0.5 mm Hg) at room temperature to give 31.82 g (92% yield) of a white solid.

G. Preparation of Prodrug 1 from Compound 7

Compound 7 (8.29 g, 10 mmol) was dissolved in a mixture of 28 mL of triethylamine and 83 mL acetonitile. After 6 hours, the reaction mixture was evaporated under vacuum and the residue was dissolved in methylene chloride. This solution was loaded onto a column of silica gel and the product Prodrug 1 was separated from cinamate 8 by elution with a gradient from pure methylene chloride to methylene chloride/methanol/water 15:10:1. The fractions containing Prodrug 1 were evaporated. The residue was dissolved in 30% iso-propanol and converted to the sodium salt by passing through a column of Dowex 50WX8 in Na$^+$ form. The material was eluted with 30% iso-propanol and evaporated under vacuum to afford an oil. This oil was crystallized from abs. ethanol, to give 4.77 g., 81% of Sodium 2-((9-Guanylyl)methyl)oxy)ethyl 1-(4-((2,2-dimethylpropionyl)oxy)-phenyl)-2-((methoxy)carbonyl) ethyl phosphate. $^1$H NMR (DMSO-d$_6$, δ): 11.40 (1H, s), 7.79 (1H, s), 7.39 (2H, m), 7.00 (3H, m), 5.38 (1H, m), 5.29 (s, 2H), 3.65 (1H, m), 3.55 (1H, m), 3.47 (3H, s), 3.03 (1H, dd), 2.72 (1H, dd) , 1.28 (9H, s) , $^{31}$P NMR (DMSO-d$_6$; 85% H$_3$PO$_4$, external reference): −0.83 (dec. on, S; dec. off, m). MW of the anion was confirmed by mass spectrometry.

An analogous synthesis was used to prepare the sodium salt of Prodrug 2, except that acetyl chloride was used in step B in place of pivoyl chloride. The structure of Prodrug 2 is shown below:

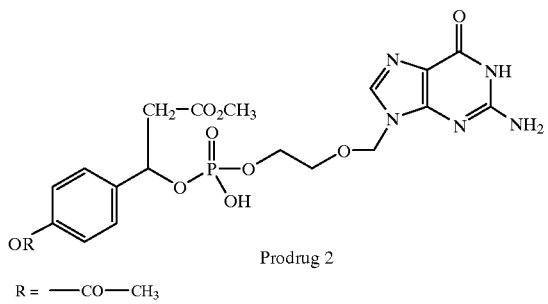

Prodrug 2

R = —CO—CH$_3$

Analytical data for Prodrug 2, sodium 2-((9-guanylyl) methyl)oxy)ethyl-1-(4-acetoxyphenyl)-2-((methoxy) carbonyl)ethyl phosphate, is as follows: $^1$H NMR (DMSO-d$_6$, δ) : 11.09 (1H, s), 7.78 (1H s), 7.36 (2H, m), 7.04 (2H, m), 6.82 (2H, broad s), 5.37 (1H, m) 5.29 (2H, s), 3.60 (2H, m), 3.49 (3H, s), 3.44 (2H, m), 2.97 (1H, dd), 2.73 (1H, dd), 2.25 (3H, s), $^{31}$P NMR (DMSO-d$_6$; 85% H$_3$PO$_4$, external reference): −5.569 (dec. on, s; dec. off, m). MS ES+548 [M+H]$^+$, ES- 524 [M-Na]$^-$.

An analogous synthesis was used to prepare the sodium salt of a third prodrug, Prodrug 3, except that diethyl carbonate was used to prepare ethyl (4-hydroxybenzoyl) acetate in step A. Thus, Prodrug 3 has the same structure as Prodrug 1, modified so that the —CH$_2$COOCH$_3$ group at the benzylic position is replace with —CH$_2$COOCH$_2$CH$_3$. Analytical data for Prodrug 3, Sodium 2-((9-guanylyl) methyl)oxy)ethyl-1-(4-((2,2-dimethylpropyonyl)oxy) phenyl)-2-((ethoxy)carbonyl)ethyl phosphate, is as follows: $^1$H NMR (DMSO-d$_6$, δ) : 11.35 (1H, s), 7.78 (1H, s), 7.38 (2H, m), 7.01 (2H, m), 6.96 (2H, broad s), 5.39 (1H, m), 5.31 (2H, s), 3.93 (2H, m), 3.64 (2H, m), 3.45 (2H, m), 3.06 (1H, dd), 2.70 (1H, dd), 1.30 (9H, s), 1.05 (3H, t), $^{31}$P NMR (DMSO-d$_6$; 85% H$_3$PO$_4$, external reference): −1.511 (dec. on, s; dec. off, m). MS ES+626 [M+Na]$^+$

EXAMPLE 3

Acyclovir Prodrug 2 is more Effective in Reducing Dermal HSV-1 Virus Infection than Acyclovir Prodrug 2 was formulated as described in Example 1. One Hartley guinea pig was inoculated with HSV-1 as described in Example 1. The guinea pig was treated with Prodrug 2 according to the protocol used in Example 1 for Prodrug 1. A comparable reduction in lesion number, lesion area and in skin viral titers was obtained with Prodrug 2 as was observed in Example 1 with Prodrug 1.

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A method of treating an individual with a viral infection, comprising administering to the individual a therapeutically effective amount of a prodrug represented by the following structural formula:

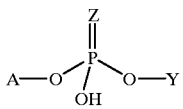

and physiologically acceptable salts thereof; wherein Z is oxygen or sulfur;

Y is, together with a hydroxy group, acyclovir or an acyclovir analog; and

A is a substituted benzyl derivative with one or more protected phenol or protected amine groups in the ortho or para positions, relative to the phosphoester, which can be converted in vivo to a hydroxy or amino group.

2. The method of claim 1 wherein Y is represented by the following structural formula:

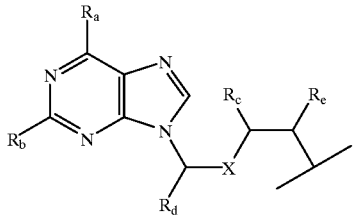

and physiologically acceptable salts thereof;

wherein:

X is sulphur, —NH—, —N(lower alkyl)— or oxygen;

R$_a$ is hydrogen, halogen, hydroxy, (lower alkyl)—O—, azide, thio, (lower alkyl)thio, amino, (lower alkyl) amino or di(lower alkyl)amino;

R$_b$ is hydrogen, halogen, (lower alkyl)thio, (lower alkyl)—CO—N—, amino or azide;

R$_c$ is hydrogen, lower alkyl, substituted lower alkyl, aryl and substituted aryl;

R$_d$ is hydrogen or lower alkyl;

R$_e$ is hydrogen, lower alkyl, substituted lower alkyl, aryl, substituted aryl, (lower alkyl)O—, (substituted lower alkyl)O—, aryloxy and substituted aryloxy; and A is a substituted benzyl derivative with one or more protected phenol or protected amine groups in the ortho or para positions, relative to the phosphoester, which can be converted in vivo to a hydroxy or amino group.

3. The method of claim 2 wherein the viral infection is caused by Herpes Simplex Virus.

4. The method of claim 3 wherein the viral infection is a dermal viral infection.

5. The method of claim 4 wherein the prodrug is administered topically to the dermal viral infection.

6. The method of claim 5 wherein Z and X are oxygen, $R_a$ is —OH and $R_b$ is —NH$_2$.

7. The method of claim 6 wherein $R_c$, $R_d$ and $R_e$ are each —H.

8. The method of claim 7 wherein the one or more groups in the para or ortho positions of A relative to the phosphoester are selected from the-group consisting of $R_8$—O—CO—O—, $R_8$NH—CO—O—, and $R_8$CO—O—, wherein $R_8$ is selected from the group consisting of lower alkyl, substituted lower alkyl, aryl, and substituted aryl.

9. The method of claim 8 wherein the benzyl group is α-substituted by a moiety such that cleavage of the phosphoester bond between A and a phosphate oxygen will result in an elimination reaction to form a carbon-carbon double bond between the α-carbon and the moiety.

10. The method of claim 9 wherein the one or more groups in the para or ortho positions relative to the phosphoester are (lower alkyl)CO—O—.

11. The method of claim 7 wherein A is of the formula:

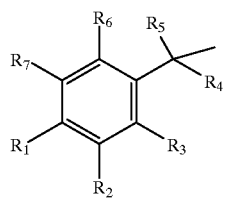

wherein:

$R_1$, $R_3$ or $R_6$ are independently selected from the group consisting of —H, —O—CO—$R_8$, —O—CO—O$R_8$, —O—C(O)—NH$R_8$, —O—C(O)—N($R_8$)$_2$, —NH—CO—$R_8$⁻, —NH—CO—O$R_8$, —NH—CO—NH$R_8$ and an inert group, with the proviso that at least one of $R_1$, $R_3$ or $R_6$ is not an inert group;

$R_2$ and $R_7$ are hydrogen —O—CO—$R_8$, or an inert group and may be the same or different;

$R_4$ and $R_5$ are independently selected from the group consisting of hydrogen, an alkyl group, a substituted alkyl group and a moiety such that cleavage of the phosphoester bond between A and a phosphate oxygen results in an elimination reaction to form a carbon-carbon double bond between the benzylic position of A and the moiety; and $R_8$ is selected from the group consisting of an alkyl group, a substituted alkyl group, an aryl group, a substituted aryl group, and a group such that the resulting ester, carbonate, amide, carbamate or urea moiety is degraded to the free hydroxy group or free amine group in vivo.

12. The method of claim 11 wherein at least one of $R_1$, $R_3$ or $R_6$ is a (—O—CO—$R_8$) group.

13. The method of claim 12 wherein $R_4$ is selected from the group consisting of —CH$_2$COOR", —CH$_2$COR", —CH$_2$CONH$_2$, —CH$_2$CONHR", —CH$_2$NO$_2$, —CH$_2$SO$_2$R" and —CH$_2$CN, wherein R" is selected from the group consisting of —H, lower alkyl, substituted lower alkyl, aryl and substituted aryl.

14. The method of claim 13 wherein $R_4$ is a (—CH$_2$—CO$_2$—R") group.

15. The method of claim 14 wherein R" is selected from the group consisting of —H, methyl, ethyl, n-propyl, iso-isopropyl, n-butyl, sec-butyl, t-butyl or —(CH$_2$)$_n$CH$_3$, wherein n is 4, 5, 6, 7, 8, 9, 10, 11, 12, 13, 14, 15, 16, 17, 18, 19 or 20.

16. The method of claim 15 wherein $R_1$ is a (—O—CO—$R_8$) group.

17. The method of claim 16 wherein $R_8$ is selected from the group consisting of methyl, ethyl n-propyl, iso-isopropyl, n-butyl, sec-butyl, t-butyl, n-pentyl, n-hexyl, CH$_3$—CO—CH$_2$—, CH$_3$O— (CH$_2$)$_2$—O—(CH$_2$)$_2$-O-CH$_2$—, CH$_3$O—(CH$_2$)$_2$—O—CH$_2$—, —OCH$_3$ —CR$_9$—NHR$_{10}$, —CH(OR$_{11}$)—CH$_3$ and —CH$_2$OR$_{11}$;

wherein:

$R_9$ is the side chain of an amino acid;

$R_{10}$ is —H or an amine protecting group; and $R_{11}$ is —H or an alcohol protecting group.

18. A method of treating an individual or animal with a viral infection, comprising administering to the individual a therapeutically effective amount of a prodrug represented by the following structural formula:

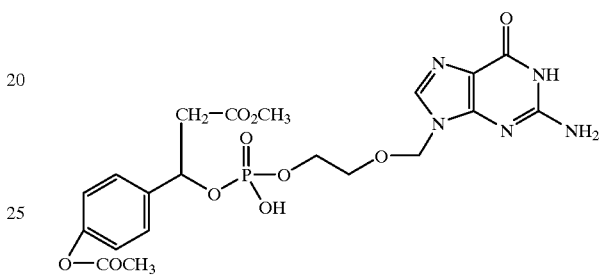

and physiologically acceptable salts thereof.

19. A method of treating an individual or animal with a viral infection, comprising administering to the individual a therapeutically effective amount of a prodrug represented by the following structural formula:

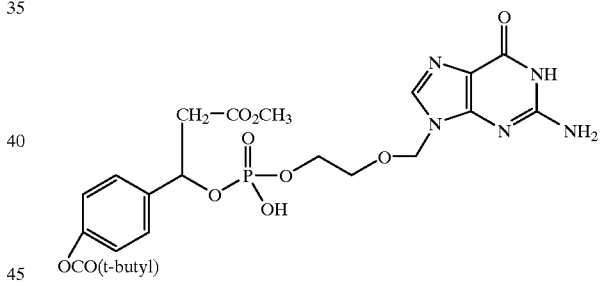

and physiologically acceptable salts thereof.

20. A method of preparing a compound represented by the following structural formula:

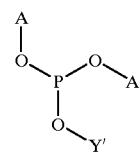

wherein:

Y' is, together with a hydroxy group, a nucleoside analog; and

A is a substituted benzyl group with one or more protected hydroxy or protected amine groups in the ortho or para positions, relative to the phosphite ester which can be converted in vivo to a hydroxy or amino group;

comprising reacting Y'—OH, a weak anhydrous organic acid and (A—O)$_2$—P(NR$_{21}$R$_{22}$) in an aprotic polar organic solvent, wherein $R_{21}$ and $R_{22}$ are each independently a lower alkyl, a substituted lower alkyl group, an aryl group, a substituted aryl group or, taken together with the phosphoramide nitrogen, are a substituted or unsubstituted five, six or seven membered nitrogen-containing heterocyclic ring.

* * * * *